US00PP11471P

United States Patent [19]

van Rijn

[11] Patent Number: Plant 11,471

[45] Date of Patent: Aug. 1, 2000

[54] ANTHURIUM PLANT NAMED 'CLAUDIARIJN'

[75] Inventor: Leonardus van Rijn, Schipluiden, Netherlands

[73] Assignee: RijnPlant B.V., Schipluiden, Netherlands

[21] Appl. No.: 09/177,594

[22] Filed: Oct. 22, 1998

[51] Int. Cl.[7] ..... A01H 5/00

[52] U.S. Cl. ..... Plt./365

[58] Field of Search ..... Plt./365, 369

[56] References Cited

U.S. PATENT DOCUMENTS

P.P. 10,706 11/1998 van Rijn ..... Plt./365

OTHER PUBLICATIONS

Gloria Simon; Evaluation of Seven (7) Dutch Cultivars of Anthurium Andraeanum Under Local Conditions; Annual Seminar on Agricultural Research: Agriculture in a Changing Economic Environment; Abstract, 1993.

*Primary Examiner*—Howard J. Locker
*Assistant Examiner*—Kent L. Bell
*Attorney, Agent, or Firm*—C. A. Whealy

[57] ABSTRACT

A distinct cultivar of Anthurium plant named 'Claudiarijn', characterized by its upright, outwardly arching and very freely clumping growth habit; durable dark green leaves that are ovate in shape; numerous inflorescences that are positioned upright and above the foliage on strong and erect scapes; durable red spathes; year-round continuous flowering; and good post-production longevity.

2 Drawing Sheets

BACKGROUND OF THE INVENTION

The present invention relates to a new and distinct cultivar of Anthurium plant, botanically known as *Anthurium andraeanum*, and hereinafter referred to by the cultivar name 'Claudiarijn'.

The new Anthurium is a product of a planned breeding program conducted by the Inventor in Schipluiden, The Netherlands. The objective of the program is to create new Anthurium cultivars that have a freely clumping growth habit, strong plant growth, attractive spathe color, numerous inflorescences and leaves, and good post-production longevity.

The new Anthurium originated from a cross by the Inventor on Feb. 21, 1992 of the Inventor's proprietary *Anthurium andraeanum* selection code number 90-3 as the female, or seed, parent with the Inventor's proprietary *Anthurium andraeanum* selection code number 90-6 as the male, or pollen, parent. The cultivar 'Claudiarijn' was discovered and selected by the Inventor as a plant within the progeny of the stated cross in a controlled environment in Schipluiden, The Netherlands in May, 1994.

Asexual propagation of the new cultivar by tissue culture in a laboratory in Belgium has shown that the unique features of this new Anthurium plant are stable and reproduced true to type in successive generations of asexual propagation.

BRIEF SUMMARY OF THE INVENTION

The new Anthurium has not been observed under all possible environmental conditions. The phenotype may vary somewhat with variations in environment such as temperature and light intensity, without, however, any variance in genotype.

The following traits have been repeatedly observed and are determined to be the unique characteristics of the cultivar 'Claudiarijn'. These characteristics in combination distinguish 'Claudiarijn' as a new and distinct cultivar:

1. Upright, outwardly arching and freely clumping growth habit.

2. Durable dark green leaves that are ovate in shape.

3. Numerous inflorescences that are positioned upright and above the foliage on strong and erect scapes.

4. Durable red spathes.

5. Year-round continuous flowering.

6. Good post-production longevity.

The new Anthurium can be compared to the female parent, the Inventor's proprietary selection code number 90-3. In side-by-side comparisons conducted by the Inventor in Schipluiden, The Netherlands, plants of the new Anthurium differ from plants of selection code number 90-3 in the following characteristics:

1. Plants of the new Anthurium have darker red spathes than plants of the selection code number 90-3.

2. Plants of the new Anthurium are more compact than plants of the selection code number 90-3.

3. Plants of the new Anthurium have more durable leaves than plants of the selection code number 90-3.

4. Plants of the new Anthurium have more durable and smaller spathes than plants of the selection code number 90-3.

The new Anthurium can be compared to the male parent, the Inventor's proprietary selection code number 90-6. In side-by-side comparisons conducted by the Inventor in Schipluiden, The Netherlands, plants of the new Anthurium differ from plants of selection code number 90-6 in the following characteristics:

1. Plants of the new Anthurium have darker red spathes than plants of the selection code number 90-6.

2. Plants of the new Anthurium have thinner leaves with less pointed apex than plants of the selection code number 90-6.

Compared to plants of the sibling cultivar 'Cora', disclosed in U.S. Plant Pat. application Ser. No. 09/177,290, plants of the new Anthurium are taller, have larger leaves and spathes, and have lighter red-colored spathes. Compared to plants of the sibling cultivar 'Saskia', disclosed in U.S. Plant Pat. application Ser. No. 09/177,591, plants of the new Anthurium are taller and have larger leaves and spathes.

The new Anthurium can be compared to the nonpatented Anthurium cultivar 'Lisette'. In side-by-side comparisons conducted by the Inventor in Schipluiden, The Netherlands, plants of the new Anthurium differ from plants of the cultivar 'Lisette' in the following characteristics:

1. Plants of the new Anthurium have smaller and thinner spathes than plants of the cultivar 'Lisette'.

2. Plants of the new Anthurium have a redder spathe color than plants of the cultivar 'Lisette'.

3. Plants of the new Anthurium and the cultivar 'Lisette' differ in spathe form.

BRIEF DESCRIPTION OF THE PHOTOGRAPHS

The accompanying colored photographs illustrate the overall appearance of the new Anthurium, showing the colors as true as it is reasonably possible to obtain in colored reproductions of this type.

The photograph at the top of the first sheet comprises a side perspective view of typical potted plants of the cultivar 'Claudiarijn'.

The photograph at the bottom of the first sheet comprises a close-up view of a typical spathe and spadix of the cultivar 'Claudiarijn'.

The photograph on the second sheet comprises a close-up view of a typical leaf of the cultivar 'Claudiarijn'. Leaf, spathe and spadix colors in the photograph may appear different from the actual colors due to light reflectance.

DETAILED BOTANICAL DESCRIPTION

In the following description, color references are made to The Royal Horticultural Society Colour Chart except where general terms of ordinary dictionary significance are used. The following observations and measurements describe two-year old plants grown in Schipluiden, The Netherlands, in a glass greenhouse with an average day temperature of 25° C. and an average night temperature of 19° C.

Botanical classification: *Anthurium andraeanum* cultivar 'Claudiarijn'.

Parentage:

*Female parent.*—Inventor's proprietary *Anthurium andraeanum selection code number* 90-3.

*Male parent.*—Inventor's proprietary *Anthurium andraeanum* selection code number 90-6.

Propagation:

*Method.*—Typical by tissue culture.

*Time to initiate roots.*—About 70 or 84 days at 24° C. or 21° C., respectively.

*Rooting habit.*—Numerous and very strong fleshy roots.

Plant description:

*Plant shape.*—Upright, inverted triangle, symmetrical.

*Growth habit.*—Erect when young, becoming outwardly arching as plants develop. Freely clumping, bushy and dense. Appropriate for 19 to 40-cm containers.

*Plant height.*—About 80 cm from soil level to apex of pathes.

*Plant vigor.*—High.

*Growth rate.*—Rapid.

*Crop time.*—About 10 months are usually required from planting of young plants to finished plants in 19-cm containers.

*Foliage description.*—Quantity: Usually about ten leaves per clump. Length: About 28.5 cm. Width: About 18 cm. Shape: Ovate. Apex: Apiculate. Base: Auriculate to cordate, lobes not overlapping. Margin: Entire. Texture: Smooth, glabrous, leathery. Color: Young leaves upper surface: Brownish red to green. Young leaves, lower surface: Brownish red to green. Mature leaves, upper surface: 137A. Mature leaves, lower surface: Darker than 144A. Petiole: Length: About 55 cm. Color: 144A with slight anthocyanin. Geniculum: Length: About 3 cm. Color: Green with slight anthocyanin.

Inflorescence description:

*Inflorescence arrangement.*—Spathe with spadix held above the foliage. Flowering structures arise from leaf axils. Freely flowering; continuous flowering year-round; typically four to seven inflorescences per plant. Not fragrant.

*Inflorescence longevity* —Inflorescences last about six weeks under winter conditions and up to three months under summer conditions; persistent.

*Flowers.*—Quantity of flowers per spadix: Numerous, about 150. Shape: Rounded. Diameter: About 1 mm, maximum.

*Spathe.*—Length: About 11 cm. Width: About 9 cm. Height above foliage: About 20 cm. Shape: Lanceolate. Apex: Apiculate to cuspidate. Base: Auriculate to cordate: lobes not overlapping. Margin: Entire. Texture: Leathery, glabrous, very slight blistering, shiny. Color: When opening: 45A to 46A. Front surface: 45B. Back surface: 47B. After senescence: 47B to 47C.

*Spadix.*—Length: About 8 cm. Diameter: About 1 cm. Shape: Columnar. Cross section: Rounded. Longitudinal axis: Very weakly recurved. Color: Base: Creamy white with slight pink coloration. Midsection: 36D. Apex: 43C. Color, after senescence: 22A.

*Scape.*—Length: About 75 cm. Aspect: Strong and erect. Color: 144A with anthocyanin towards apex.

*Reproductive organs.*—Androecium: Pollen color: Creamy white, 158D. Gynoecium: Stigma shape: Ovoid.

Disease resistance: Plants of the new Anthurium have not been shown to be resistant to diseases common to Anthurium.

Seed development: Seed development on plants on the new Anthurium has not been observed.

It is claimed:

1. A new and distinct cultivar of Anthurium plant named 'Claudiarijn', as illustrated and described.

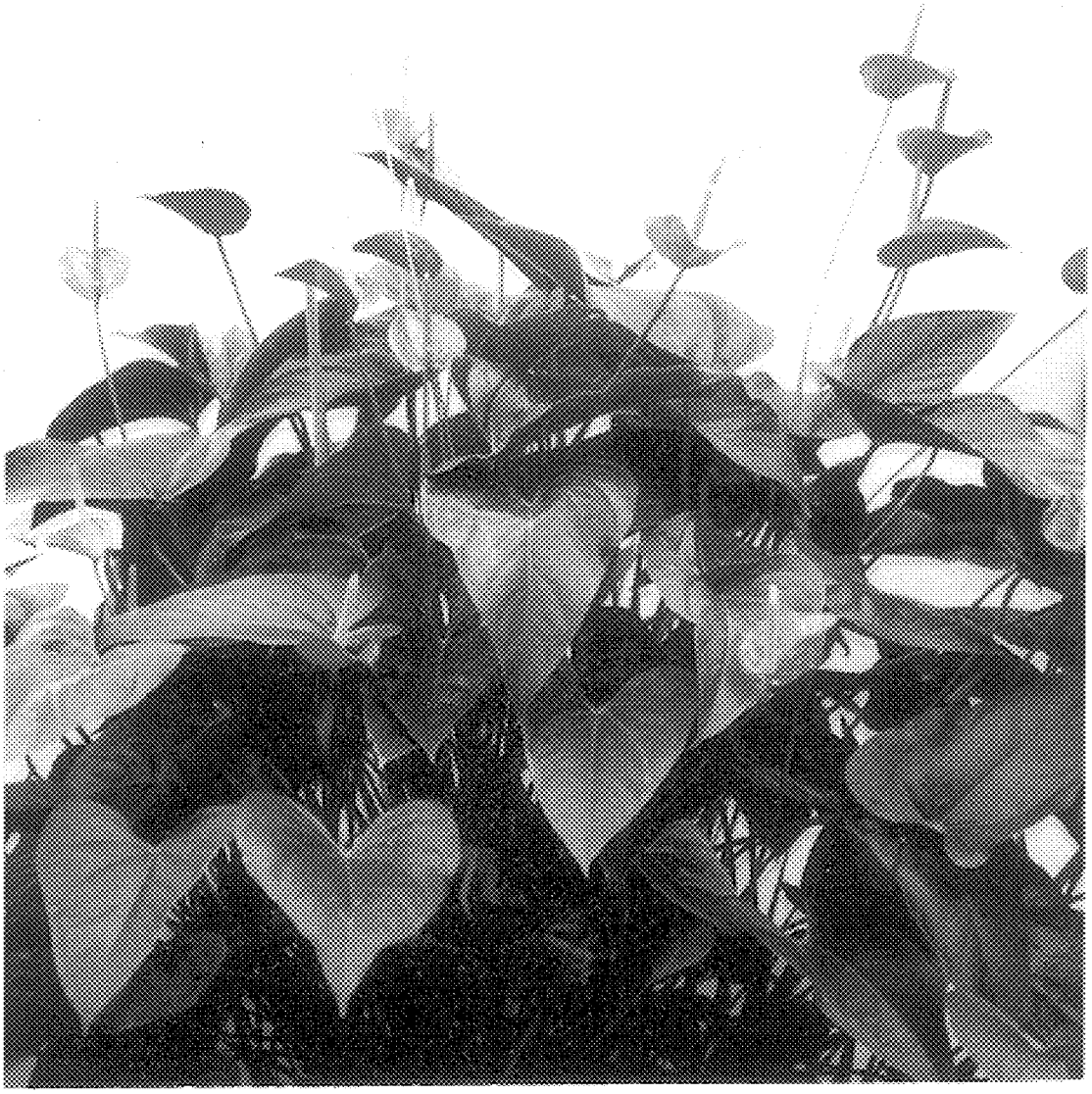
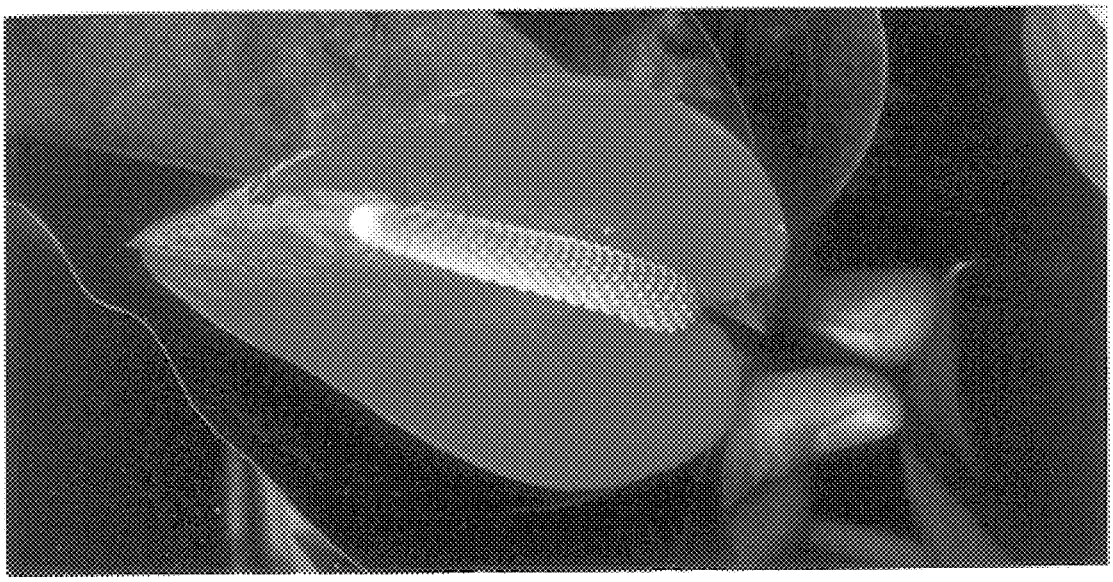

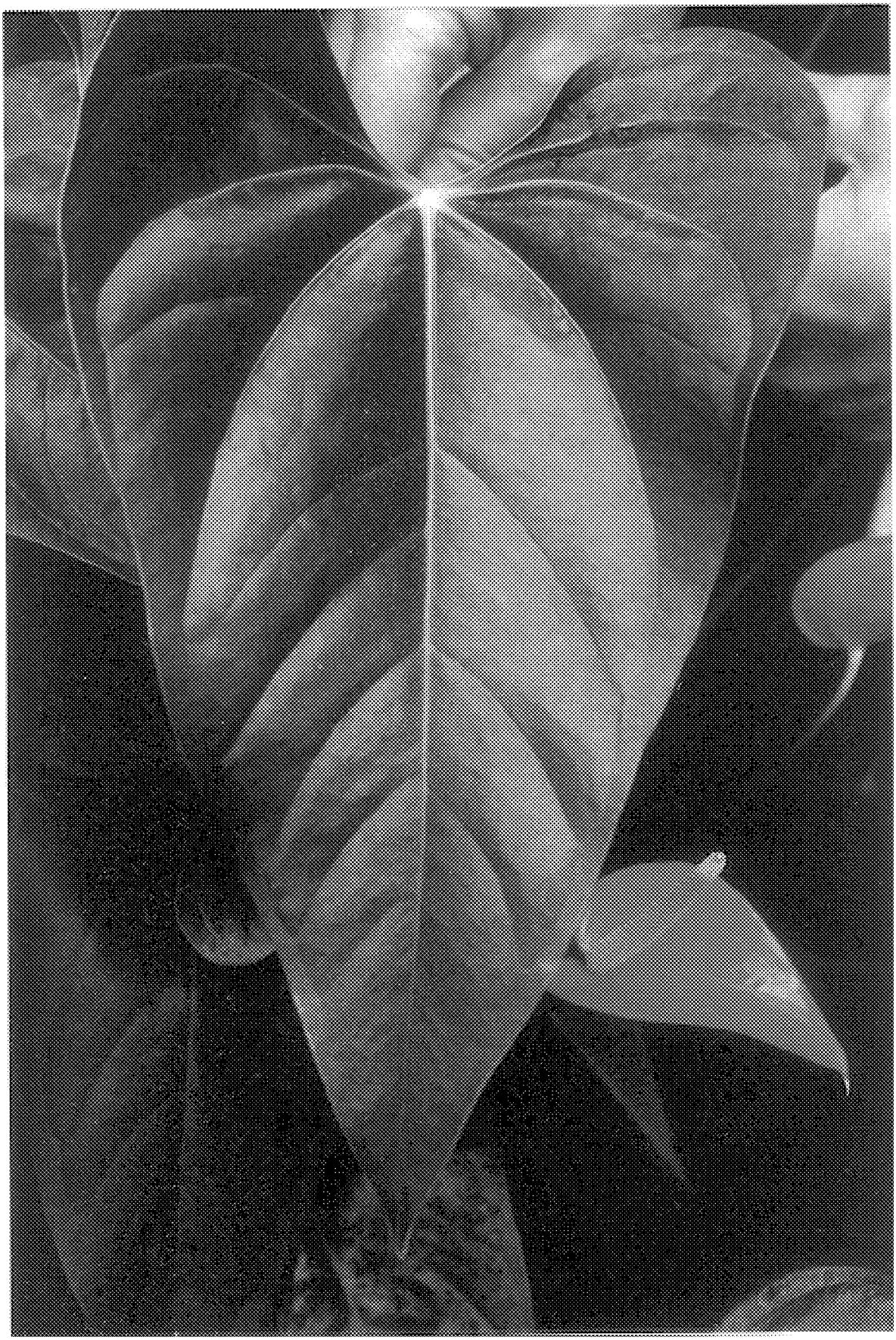

* * * * *